US005139630A

United States Patent [19]
Chen

[11] Patent Number: 5,139,630
[45] Date of Patent: Aug. 18, 1992

[54] IDENTIFICATION OF SAMPLE CONSTITUENTS UTILIZING CAPILLARY ELECTROPHORESIS

[75] Inventor: Fu-Tai A. Chen, Brea, Calif.

[73] Assignee: Beckman Instruments, Inc., Fullerton, Calif.

[21] Appl. No.: 708,424

[22] Filed: May 31, 1991

[51] Int. Cl.$^5$ .................... B01D 57/02; B01D 61/42
[52] U.S. Cl. ........................ 204/180.1; 204/299 R
[58] Field of Search .................... 204/180.1, 299 R; 356/344

[56] References Cited

U.S. PATENT DOCUMENTS

| | | | |
|---|---|---|---|
| 4,941,958 | 7/1990 | Byers | 204/299 R |
| 4,994,165 | 2/1991 | Lee et al. | 204/299 R |
| 5,021,646 | 6/1991 | Weinberger et al. | 204/299 R |

OTHER PUBLICATIONS

Fujiwara, S. & Honda, S.; "Determination of Cinnamic Acid and Its Analogues by Electrophoresis in a Fused Silica Capillary Tube"; *Anal. Chem.* 58: 1811–1814 (1986).
Otsuka, K. et al.; "Quantitation and Reproducibility in Electrokinetic Chromatography with Micellar Solutions"; *J. Chrom.* 396 350–354 (1987).
Chen, Fu-Tai A. et al.; "Capillary Electrophoresis—A New Clinical Tool"; *Clin. Chem.* 77/1:14–19 (1991).
Gordan, M. J. et al.; "Protocol for Resolving Protein Mixtures in Capillary Zone Electrophoresis"; *Anal. Chem.* 63:69–72.
Jorgenson, J. W. and Lukacs, K. D.; "Capillary Zone Electrophoresis"; *Science* 222:266–272 (1983).
Lauer, H. H. & McManigill, D.; "Capillary Zone Electrophoresis of Proteins in Untreated Fused Silica Tubing"; *Anal. Chem.* 58:166–170 (1986).
Gordan, M. J. et al.; "Protocol for Resolving Protein Mixtures in Capillary Zone Electrophoresis"; Anal. Chem. 63: 69–72, 1991.
Honda, S. et al. "Analysis of Oligosaccharides in Ovalbumin by High Performance Capillary Electrophoresis", Anal. Biochem. 191:228–234 (1990).

*Primary Examiner*—John Niebling
*Assistant Examiner*—Caroline Koestner
*Attorney, Agent, or Firm*—William H. May; P. R. Harder; Richard P. Burgoon, Jr.

[57] ABSTRACT

External markers and method for the identification of protein-and-peptide-containing samples utilizing capillary electrophoresis analysis. As disclosed, at least two external markers are added to the sample: one of the markers is a neutral charge species and one of the markers is an ionic species. Dimethylformamide is a preferred neutral charge species and benzoic acid is a preferred ionic species. Identification of constituent species is determined by comparing the migration ratios of the constituent species with migration ratios for each constituent species member.

36 Claims, 5 Drawing Sheets

IDENTIFICATION OF SAMPLE CONSTITUENTS UTILIZING CAPILLARY ELECTROPHORESIS

RELATED APPLICATIONS

The present application is related to U.S. application Ser. No. 07/708,272, entitled "ANALYSIS OF SAMPLES UTILIZING CAPILLARY ELECTROPHORESIS" filed simultaneously herewith by Fu-Tai A. Chen and James C. Sternberg, and U.S. application Ser. No. 07/708,144, entitled "QUANTIFICATION OF SAMPLES UTILIZING CAPILLARY ELECTROPHORESIS" filed simultaneously herewith by Fu-Tai A. Chen.

FIELD OF THE INVENTION

The present invention is related to analysis of samples in general, analysis by capillary zone electrophoresis in particular, and specifically to identification of sample constituents using capillary zone electrophoresis.

BACKGROUND OF THE INVENTION

The articles set forth in the Background of the Invention are each incorporated herein by reference.

Mammalian proteins present in clinical samples (e.g. whole blood, serum, plasma, cerebrospinal fluid, and urine) are useful as indicators of a disease state or a bodily condition. The amount and type of these proteins in the sample can provide a wealth of information to the clinician.

For example, the protein components of serum include albumin, alpha-1 lipoprotein, alpha-2 macroglobulin, beta-1 lipoprotein and immunoglobulins (including gammaglobulins). Albumin, the major protein of serum, is usually present in a concentration of between 4.0 and 5.0 g/dL. Decreased concentration of albumin can be indicative of renal disease; increased concentration of albumin is characteristic of dehydration. Elevated levels of alpha-1 lipoprotein can be indicative of chronic alcoholism or hyperestrogenism due to, e.g., pregnancy. Elevated levels of beta-1 lipoprotein can be indicative of increased cholesterol levels.

Mammalian proteins are charged proteins containing both cationic and anionic moieties. They thus lend themselves to analysis by capillary zone electrophoresis ("CZE"). CZE is a technique which permits rapid and efficient separations of charged substances. In general terms, CZE involves introduction of a sample into a capillary tube and the application of an electric field to the tube. The electric field pulls the sample through the tube and separates it into its constituent parts. I.e., each of the sample constituents has its own electrophoretic mobility; those having greater mobility travel through the capillary faster than those with slower mobility. As a result, the constituents of the sample are resolved into discrete zones in the capillary tube during the migration of the sample through the tube. An on-line detector can be used to continuously monitor the separation and provide data as to the various constituents based upon the discrete zones. The detector measures the absorbance of light by each constituent at a specified wavelength; different constituents absorb light differently, and, because of this, the constituents can be differentiated from each other.

CZE can be generally separated into two categories based upon the contents of the capillary columns. In "gel" CZE, the capillary tube is filled with a suitable gel, e.g. polyacrylamide gel. Separation of the constituents in the sample is predicated in part by the size and charge of the constituents travelling through the gel matrix. In "open-tube" CZE, the capillary tube is filled with an electrically conductive buffer solution. Upon application of an electric field to the capillary, the negatively charged capillary wall will attract a layer of positive ions from the buffer. As these ions flow towards the cathode, under the influence of the electrical potential, the bulk solution must flow in this direction to maintain electroneutrality. This electroendosmatic flow provides a fixed velocity component which drives both neutral species and ionic species, regardless of charge, towards the cathode. The buffer in open CZE is as stable against conduction and diffusion as the gels utilized in gel CZE. Accordingly, separations can be obtained in open CZE quite similar to those obtained in gel-based electrophoresis.

Typically, the pH of the buffers utilized in open CZE are chosen with reference to the isoelectric points (pI) of the constituents in the sample. For example, the pI of serum albumin is 4.6; therefore, at pH 4.6, negatively charged and positively charged moieties of serum albumin are equal and the overall charge is neutral. However, as the pH is raised above the isoelectric point, the negatively charged moieties predominate and the net charge is negative. Thus, by selection of the proper pH, all of the species of the sample will be negatively charged. For serum samples, at pH greater than about 8.00, the majority of all serum-protein species will be negatively charged. Thus, manipulation of the isoelectric points of sample species can be used to ensure a proper charge distribution vis-a-vis the flow of such species through a charged capillary.

Typically, the results of CZE analysis are provided via an electropherogram which depicts the discrete zones of the sample constituents as peaks of various height and width. Additionally, the results can be presented in terms of numerical data based upon the integrated area under each constituent peak.

A problem encountered with capillary zone electrophoresis of samples is that the same sample constituents may appear on the electropherogram at different migration times for different samples. Stated again, a constituent common to two different samples may show up at a different place on each of the electropherograms for such samples. This is due, in part, to the fact that the amount of time taken by each earlier sample constituent as it passes through the capillary will affect the migration time of latter sample constituents.

In order to identify the specific constituent species in the sample being analyzed, the particular shape and location of a constituent species' electropherogram peak, relative to other constituent peaks, is typically determined. Stated again, the identification of a constituent species is based upon the particular electropherogram peak generated by that species. Alternatively, identification of the constituent species is based upon the retention time of that particular species. "Retention time" is defined as the period from initiation of analysis of the sample to detection of a sample constituent by the on-line detector.

However, skill is required in visually identifying the electropherogram peaks of particular constituents or identifying a constituent species based upon its retention time. For example, gammaglobulin, beta-1 lipoprotein, alpha-1 lipoprotein, and alpha-2 macroglobulin, which are serum proteins, all have about the same retention time and about the same electropherogram peak sizes when present in normal concentrations.

Furthermore, the concentration of one species in a sample can effect the shape and location of the electropherogram peak of another species in that sample. Additionally, as the concentration of a particular constituent species changes from sample to sample, so too will the retention time of that particular species. This can hamper identification of the individual constituents because a particular constituent will not always appear at the same electropherogram location from sample to sample.

In situations where different samples obtained from the same source but at different times may evidence different constituent concentrations, or in situations where samples obtained from different sources have the same constituents but include different concentrations for these constituents, it is essential that efficient, rapid and reliable identification of the sample constituents can be made without resort to visual identification guesswork or concern as to changes in the sample which will affect the retention times of the sample constituents.

SUMMARY OF THE INVENTION

The present invention satisfies this need by adding at least two external markers to the sample to be analyzed and using the derived electropherogram peak information generated by the external markers, as well as the migration times of the constituent species, as the basis for identifying those species. For convenience, one of the markers is referred to herein as the "ionic species" and the other marker is referred to herein as the "neutral charge species."

As used herein, the term "external" in reference to a marker indicates a marker that generates a unique and well defined electropherogram peak that is not co-mingled with any other electropherogram peak, and which appears either before all of the major constituent peaks of the analyzed sample, or after all of the major constituent peaks of the analyzed sample. The electropherogram peak of the neutral charge species appears before all other eletropherogram peaks and the electropherogram peak of the ionic species appears after all other electropherogram peaks. Accordingly, the external markers "bracket" the electropherogram peaks of the sample constituents.

By "neutral charge species" is meant a species having a neutral charge. Upon ionization, species that have a neutral charge will transit the capillary faster (relative) than negatively charged species. Therefore, a neutral charge species will be detected by the on-line detector before a negatively charged species. The intent is that the neutral charge species serves as the "starting point" for measuring the time or distance between the neutral charge species and the sample constituent species and the ionic species.

By "ionic species" is meant a species having a charge density of between about 0.02 and about 0.001. "Charge density" is defined as the number of negative charges of a species divided by the molecular weight of that species. In the most preferred embodiment of the invention, the ionic species has a single negative charge, and a molecular weight of between about 50 and about 750, more preferably between about 75 and 250 and most preferably between about 100 and about 160. The ionic species is selected relative to the charge density of the constituents of the sample transiting the capillary column such that the charge density of the ionic species is greater than the that of each of the major constituents of the sample.

Identification of each constituent species is based upon the migration ratio of each species. The "migration ratio" is defined as the quotient obtained from the value derived from the subtraction of the migration time of the neutral charge species from the migration time of a constituent species, divided by the value derived from subtraction of the migration time of the neutral charge species from the migration time of the ionic species. I.e., the foregoing may be symbolically represented as follows:

$$C.S._{MR\%} = \frac{(C.S. - R)}{(S - R)} * 100\%$$

where "$C.S._{MR\%}$" is the migration ratio percentage of a constituent species; "C.S." is the migration time of a constituent species; "S" is the migration time of the ionic species; and "R" is the migration time of the neutral charge species. As used throughout the disclosure, the symbol "*" is meant to indicate a mathematical multiplication symbol.

These and other advantages will be set forth in detail in the following detailed disclosure.

DETAILED DESCRIPTION OF PREFERRED EMBODIMENTS

Figure 1:
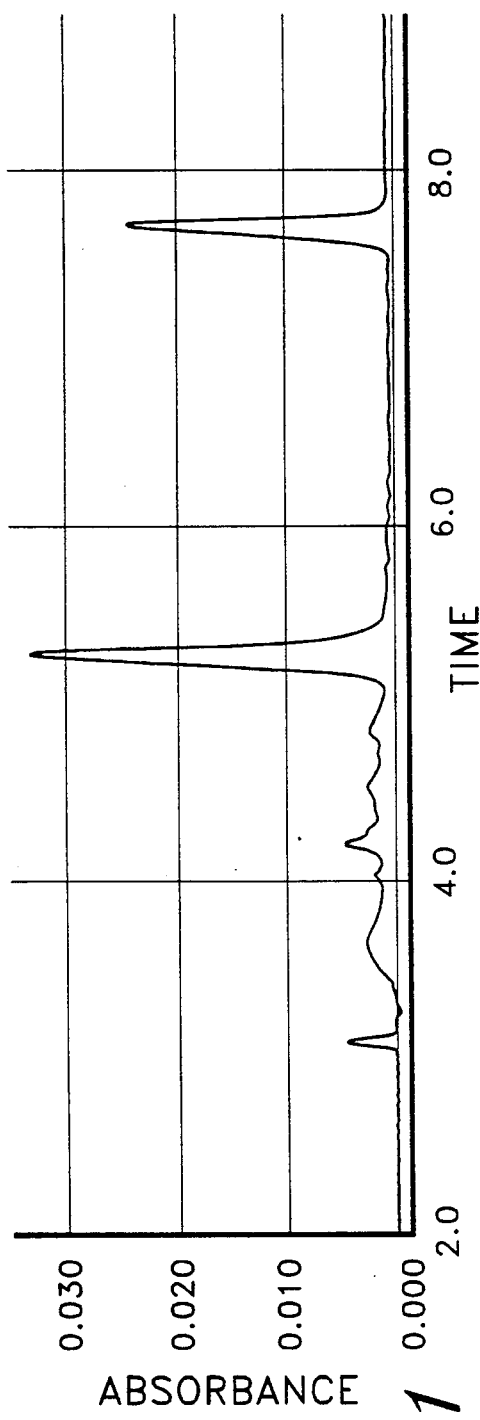
FIG. 1 is an electropherogram of a normal serum protein control to which external markers dimethylformamide (neutral charge species) and benzoic acid (ionic species) have been added, separated into its constituent parts.

For simplicity of presentation this portion of the disclosure is directed to identification of clinical samples. It is understood, however, that the present invention is equally applicable to identification of peptide-containing samples and protein-containing samples other than clinical samples, as well as samples containing native/natural or synthetic RNA, or native/natural or synthetic DNA.

The problems of identifying constituents by visually comparing constituent electropherogram peaks or by reliance upon retention times are avoided by the present inventive method of adding at least two external markers to the sample to be analyzed.

One external marker, referred to as the "neutral charge species," is selected to be detected before any of the constituents of the sample. It can thus be used to determine flow rate and provide an indication that the system is properly working. I.e., a deviation from this pattern would be an indication of a problem with the system, and, equally important, with that particular analysis (i.e. the sample would have to be re-analyzed).

The other external marker, referred to as the "ionic species," is selected to have a charge density greater than that of the last major constituent of the sample being analyzed. It will thus pass the on-line detector and appear as a peak on the resultant electropherogram after most, if not all, of the sample constituents.

A. The Neutral Charge Species

The neutral charge species is detected before the constituent species and the ionic species. The neutral charge species thus serves as a "landmark" to indicate the imminent arrival of the sample constituents. This is because negatively-charged species proceed through the capillary more slowly than neutral charged species. As noted, upon ionization or when pH is greater than pI, the constituent species will be negatively charged. Additionally, because the neutral charge species proceeds through the capillary irrespective of the amount or type of sample to be analyzed, i.e. because it is first and hence will not be impeded or its flow rate affected by any of the sample constituents, it can be used to determine the flow rate of the sample. Equally as important, if a sample constituent peak appears before the neutral charge species, this is indicative of a system problem, e.g., the pH of the buffer may be below pI, or the capillary may not be clean, etc.

As previously noted, the pH of the buffers used in open CZE are chosen with reference to the isoelectric points of the constituents of the sample. The objective is to determine the pH at which all of the constituents will be negatively charged. For serum, this is a pH greater than about 8.00. Thus, the neutral charge species should be stable in aqueous solutions having a pH of at least about 8.00. It is also desirable for the neutral charge species to have absorbance characteristics similar to those of peptide bonds so that the neutral charge species will be detected by the on-line detector along with the sample constituents. This is because the constituents of clinical sample are comprised of protein species, and protein species include peptide bonds. Thus, the neutral charge species preferably has an absorbance of less than about 300 nm, more preferably less than about 250 nm, and most preferably between about 220 nm and about 200 nm.

The particular structural conformation of the neutral charge species is not, in and of itself, important. Thus, cyclic-, straight chain-, or branched-neutral charge species having the required neutral charge can be used.

The neutral charge species, which has a neutral charge upon ionization, can be separated into two sub-groups. The first sub-group is referred to herein as "non-peptide" neutral charge species. Examples include mesityl oxide, isopropanol, methanol, ethanol, and ethylene glycol. Of these, mesityl oxide is preferred. The second sub-group is referred to herein as "peptide" neutral charge species. These include at least one peptide bond. The peptide neutral charge species are preferred because their absorbance characteristics are much more akin to that of protein species. Examples of peptide neutral charge species include dimethylformamide ("DMF"), formamide and "protected" peptides (i.e. neutral charge peptides) such as, for example, the N-acetyl-methyl ester of glycine. As used herein, a "protected" peptide is one that is not a charged moiety but maintains a neutral charge. Amino acids can also be utilized as peptide neutral charge species as long as its amino group is protected as defined.

DMF, a peptide neutral charge species, is the most preferred neutral charge species due to its solubility, absorbance characteristics, availability and relatively low cost.

The concentration of the neutral charge species added to the sample should not be greater than about 0.050% by volume. Preferably, the concentration of the neutral charge species is not greater than about 0.025% by volume, more preferably not greater than about 0.015% by volume, and most preferably about 0.002% by volume.

A second ionic species can also be used as the neutral charge species. In such a situation, the charge density (to be described in detail below) of the second ionic species is selected such that it proceeds through the capillary faster than the sample constituents. I.e., the charge density of the second ionic species is less than the charge density of the first major constituent of the sample being analyzed.

B. The Ionic Species

The ionic species is an external marker that it is detected after the last major component of the analyzed sample. As such, the principal criteria for the ionic species is the location of its electropherogram peak relative to that of the sample constituents. Thus, the ionic species should have a "flexible" flow rate, i.e. the ionic species should be able to, in effect, adapt to the sample by "lagging behind" the last sample constituent zone, irrespective of the deviation in sample volume or conditions. This criteria for the ionic species is determined by the "charge density" of the ionic species.

The charge density is a measure of the "speed" at which either a constituent in the sample being analyzed, or the ionic species, will travel through the capillary. A constituent having a higher charge density will migrate more slowly through the capillary compared to a constituent having a lower (relative) charge density. If the ionic species is to pass the on-line detector after the last sample constituent, then the charge density of the ionic species must be greater than the charge density of the last sample constituent.

The "charge density" of a species is defined as the number of negative charges of a species divided by the molecular weight of that species. The charge density of the ionic species is preferably between about 0.02 and about 0.001, more preferably between about 0.01 and about 0.004, and most preferably between about 0.01 and about 0.006. In the most preferred embodiment of the present invention, the ionic species has a single negative charge such that its molecular weight is preferably between about 50 and about 750, more preferably between about 75 and about 250, and most preferably between about 100 and about 160. However, the ionic species can have several negative charges; as the number of negative charges are increased, the molecular weight of that species must also increase such that the charge density continues to be within the desired range of from about 0.02 to about 0.001.

The negative charge of the species is dereived from a "negative charge moiety" of that species. By "negative charge moiety" is meant either at least one carboxylic acid moiety, or at least one sulfonic acid moiety, or at least one phosphoric acid moiety, or at least one phenylate moiety, or at least one thiophenylate moiety. Upon ionization or when pH is greater than the pI, these moieties will be negatively charged. As is appreciated by those in the art, phosphoric acid has from between 1 and 3 negative charges. Under acidic conditions (i.e. about pH 4), phosphoric acid has a single negative charge; under neutral conditions (i.e. pH about 7), phosphoric acid has two negative charges; and under basic conditions (i.e. pH of about 9), phosphoric acid has three negative charges.

The ionic species, as with the neutral charge species, preferably has absorbance characteristics similar to those of peptide bonds, as well as stability characteristics in aqueous solutions having a pH of at least about 8.0.

The particular structural conformation of the ionic species is not, in and of itself, important. Thus, cyclic-, straight chain-, or branched-ionic species having the required negative charge moiety can be used, provided that they have a charge density between about 0.02 to about 0.001.

Examples of ionic species include formic acid (1 negative charge; molecular weight of 48; charge density of 0.02), acetic acid (1;60;0.017), benzophosphoric acid (2;158;0.013), propionic acid (1;74; 0.014), isopropionic acid (1;74;0.014), butyric acid (1;88;0.011), isobutyric acid (1;88;0.011), benzoic acid (1;122;0.008), benzo-sulfonic acid (1;148;007), orthochloro benzoic acid, metachloro benzoic acid, and parachloro benzoic acid, (1;157;0.006), naphthyl sulfonic acid (1;208;0.005), benzo-naphthalinic acid (1;224;0.004), chloro-benzo naphthalinic acid (1;258:0.004), chloronaphthyl sulfonic acid (1;242;0.004), tetra-iodo benzo naphthyl sulfonic acid (1;716;0.001), and di-iodo anthracenyl sulfonic acid (1;776;0.001). Most preferably, benzoic acid is utilized as the ionic species.

The amount of the ionic species added to the sample is based upon a combination of the desired integrated area for the ionic species; the dilution of the sample; the protein concentration from a normal control; and an absorbance value derived from fixed volume amounts of the ionic species and the sample.

The integrated area of the electropherogram ionic species peak should be less than about 50% of the total integrated area for the sample constituent peaks and the ionic species peak. This is because the integrated area of the ionic species should not be so great as to diminish the integrated areas of the sample constituents; an integrated area for the ionic species peak of greater than about 50% would cause such a diminishing affect on the other electropherogram peaks. Preferably, the integrated area should be between about 5% and about 40% of the total integrated area, and most preferably about 30% of the total integrated area.

CZE analysis usually involves dilution of the sample being analyzed. For example, serum, plasma, and whole blood are diluted prior to introduction to the capillary in order to assist these samples in flowing through the capillary; urine and cerebro-spinal fluid can be diluted, but dilution is not a requirement. Dilution is typically from about 1 part sample to about 20 parts diluent (1:20=0.05), to about 1:100 (0.01). Most preferably where dilution is desirable, the dilution ratio is 1:50 (0.02). Diluents which can be used and which are applicable to the present invention are well known and varied and will not be discussed herein. However, an example of such a diluent is ICS TM Diluent (Beckman Instruments, Inc.). The diluent should preferably have a neutral pH (i.e. about 7).

The protein concentration from a control is selected to have a concentration of protein equal to that normally present in a typical normal human sample. For example, the protein concentration from a serum sample of a healthy individual is about 60 mg/ml. Similar concentration values for urine and cerebrospinal fluid ("CSF") are about 10 $\mu$g/ml and between about 150 and 400 $\mu$g/ml, respectively. Thus, if a patient serum protein concentration is above or below these normal values, a clinical problem may exist. For consistency of concentration terms, the protein concentration present in human serum is about 60,000 $\mu$g/ml.

A further factor needed in the determination of the amount of ionic species added to the sample is based upon the absorbance of defined amounts of the ionic species and the sample at the fixed wavelengths detected by the on-line detector. When a defined amount of the ionic species and the sample are irradiated with light at a fixed wavelength, a numerically defined absorbance value for each can be determined. These two values are used to provide a ratio of absorbance for the ionic species alone and the sample alone. These values are obtained separately so as to determine the absorbance characteristics of each without interference from the other.

In order to determine the amount of the ionic species to be added to the sample ("I.S"), the above factors are mathematically manipulated by multiplying the normal protein concentration of the particular sample being analyzed by the dilution factor (for CSF, a mid-point value of 275) $\mu$g/ml can be used for the protein concentration); this value is then multiplied by the desired integrated area of the ionic species; finally, the total is multiplied by: the quotient derived from the absorabance value of a defined amount of the ionic species measured at a fixed wavelength divided by the absorbance value of the same defined amount of the sample measured at about the same fixed wavelength.

The foregoing may be symbolically represented as follows:

$$I.S. = (S * D * P.W.) * X/Y \qquad (1)$$

In this equation, "S" is the desired integrated area percentage of the ionic species peak as defined above; "D" is the dilution factor of the sample as defined above (for samples that are not diluted such as urine or cerebro spinal fluid, this value can be 1.0); "P.W." is the normal protein concentration; "X" is the absorbance of (most preferably) 100 μg/ml of the ionic species at a fixed wavelength; and "Y" is the absorbance of 100 μg/ml of sample at a fixed wavelength. X and Y are typically expressed in nanometers. With respect to the absorbance values and the amount of ionic species and sample measured, the particular amount is not of import per se; what is important is that the amounts utilized for both the sample and the ionic species be about the same.

Clinical samples include peptide and protein species. Peptides and proteins are made from an assortment of 20 amino acids. Each amino acid has a side chain. One method of catagorizing amino acids is based upon whether these side chains are acidic, basic, uncharged-polar or non-polar. Lysine, arginine and histidine have basic side chains; asparagine, glutamine, serine, threonine and tyrosine have uncharged-polar side chains; glycine, alanine, valine, leucine, isoleucine, proline, phenylalanine, methionine, tryptophan, and cysteine have non-polar side chains; and aspartic acid and glutamic acid have acidic side chains. Of the 20 amino acids, only aspartic acid and glutamic acid, because of their acidic side chains, will maintain a net negative charge upon ionization.

Accordingly, while charge density is defined as the number of negative charges of a species divided by the molecular weight of that species, the charge density of peptides, proteins and native and/or synthetic DNA or RNA can also be determined by dividing the number of aspartic acid and glutamic acid amino acids in these species by the molecular weight of that species.

For efficiency and speed of analysis, it is desirable to utilize an ionic species which is detected within a relatively brief period after the detection of the last sample constituent. "Relatively brief" is defined as less than about two minutes; longer times may, however, also be used.

C. Identification of Constituent Species

A CZE electropherogram is most typically presented with Time plotted along the horizontal, or, "X", axis, and Absorbance plotted along the vertical, or, "Y", axis. Thus, each constituent species is differentiated as a function of its detected absorbance of light over the period of time necessary for complete detection of the species by the on-line detector. A specified "migration time" for each constituent species can be ascertained from the CZE electropherogram analysis. The "migration time" of a constituent species and the ionic species is defined as the period between the migration of that species from the detection of the neutral charge species until detection of that species by the on-line detector The "neutral charge species' migration time" is defined as the period between initiation of analysis of the sample until detection of the neutral charge species. As used herein, the term "period" connotes both actual time and a measured distance as derived from the electropherogram.

Identification of each constituent species is based upon the "migration ratio" of such species. The migration ratio is defined as the quotient obtained from the value derived from the subtraction of the migration time of the neutral charge species from the migration time of a constituent species, divided by the value derived from subtraction of the migration time of the neutral charge species from the migration time of the ionic species. The migration ratio may be multiplied by 100% so as to provide a migration ratio percentage.

The foregoing may be symbolically represented as follows:

$$C.S._{MR\%} = \frac{(C.S. - R)}{(S - R)} \cdot 100\%$$

where "$C.S._{MR\%}$" is the migration ratio percentage of a constituent species; "C.S." is the migration time of a constituent species; "S" is the migration time of the ionic species; and "R" is the migration time of the neutral charge species.

The migration ratio normalizes each constituent species' migration time relative to the total migration time between the neutral charge species and the ionic species. As used herein, the term "normalize" indicates that the migration time of each constituent species is calibrated based upon a common factor, i.e., the migration time difference between the ionic species and the neutral charge species.

Thus, once a constituent species' migration ratio is defined, then irrespective of the concentration of same-sample constituent species, subsequent migration ratios for same-sample constituent species will have the same or substantially the same migration ratio. As used herein, the term "same-sample" indicates the same type of sample, for example, human serum samples that are from different patients or human serum samples that are from the same patient but obtained at different time periods. Thus, irrespective of the protein concentration in a given sample, or the amount of migration time required to analyze a given sample, the constituent species can be identified with precision. As used herein, the term "substantially the same" migration ratio means plus-or-minus about 30%, preferably about 20% and most preferably about 15% of a constituent species' migration ratio.

EXAMPLES

The following examples directed to preferred embodiments of the invention disclosed herein are not intended, nor should they be construed, as limiting the disclosure, or the claims to follow.

A. Materials and Methods

I. Capillary Electrophoresis Procedures

Capillary electrophoresis of clinical samples and controls were performed on a Beckman Instruments, Inc. high performance capillary electrophoresis system (Beckman Instruments, Inc., Fullerton, Calif., USA, Model No. 357575). Data analysis was performed on System Gold™ software (Beckman Instruments, Inc.). The aforementioned capillary electrophoresis system contains built-in 214, 254, 280 and 415 nm narrow-band filters for on-line detection. Electrophoresis was performed in a fused silica tube, 75 μM i.d. and 25 cm long (Polymicro Technologies, Inc., Phoenix, Ariz. USA, Product No. TSP075375). The detection window was located approximately 6.5 cm from the column outlet.

Clinical samples and controls were placed on the inlet tray of the above-described capillary electrophoresis system. Clinical samples and controls were automatically injected into the capillary tube by the electrokinetic method for 3 to 10 seconds at 1 kV. Analysis was performed in less than 10 minutes using a column voltage gradient of 200 volts/cm. The capillary tube was washed and reconditioned between each run (18 seconds in NaOH, 12 seconds 0.1% Triton-X 100 ™ in distilled H₂O).

II. Electrophoresis Buffer

Electrophoresis buffer was made in accordance with the disclosure of the co-pending application referenced above, by dissolving 9.95 g of boric acid (MW 61.83) and 4.86 g sodium hydroxide (MW 40.00) in 1L distilled H₂O. Final concentration of boric acid was 80 mM/L and final pH was adjusted to 10.25±0.1 by dropwise addition of 1N NaOH.

III. Reagents

All chemicals were at least of ACS grade. Benzoic acid (Aldrich Chemical, Milwaukee, Wis., USA, Part No. 24,238-1) and DMF (Aldrich Chemical, Part No. 22,705-6) were added to ICS ™ Diluent (Beckman Instruments, Inc., Part No. 449690) such that the final benzoic acid concentration was 0.10 mg/ml and the percent by volume of DMF to the diluent was 0.002%; an example of how the benzoic acid concentration was derived will be set forth in Example II. Protein ionic species utilized for normal and abnormal controls was I.D. - Zone ™ Normal Protein Electrophoresis Control (Beckman Instruments, Inc., Part No. 667600). A 1:50 protein control:diluted marker ratio was utilized.

Patient serum samples were obtained from Harbor General Hospital, Torrance, Calif. A 1:50 serum sample:diluted marker ratio was utilized.

B. Examples

Example I

Protein Charge Density Estimation

The charge density for the protein species can be readily and effectively calculated for purposes of determining the charge density of the ionic species either by a determination of the number of aspartic acid and glutamic acid amino acids in the protein, as outlined above, by conventional sequencing techniques such as, for example, the Sanger-Coulson or Maxam-Gilbert methods, or by protein sequencing instruments, such as, for example, the PI 2020 ™ and PI 2090E ™ protein sequencers (Porton Instruments, Inc., Tarzana, Calif.)

Folowing the outlined procedure, for example, the last major component of human serum to be detected by CZE analysis is albumin (pre-albumin is the absolute last component of serum). Serum albumin (human) has a molecular weight ("MW") of about 86,000. Each amino acid has an approximate molecular weight of about 100. Therefore, for human serum albumin ("HSA"):

$$\frac{86,000 \text{ MW}}{100 \text{ MW}/a.a.} = 860 \text{ amino acids}$$

Thus, there are approximately 860 amino acids in HSA. Theoretically, because there are twenty amino acids in HSA, approximately five percent of the HSA amino acids should be aspartic acid, and approximately five percent should be glutamic acid; i.e. 10% of the approximate 860 HSA amino acids should have a net negative charge upon ionization. However, for calculation purposes, it is considered prudent to double this theoretical approximation to 20% in order to estimate a theoretical maximum negative charge. Doubling the contribution of negatively charged moieties to the constituent will not impose a deleterious impact upon the amount of ionic species utilized. Therefore, for purposes of calculation, in order to determine the approximate charge density of HSA:

20% × 860 a.a. = 172 carboxylic acid moieties $$\frac{172}{86,000 \text{ MW}} = \frac{1}{500} = .002 = \text{approximate charge density of } HSA$$

Therefore, for the ionic species to travel slower than the last sample constituent, in this case, HSA, the charge density of the ionic species must be greater than 0.002.

The foregoing methodology can be readily utilized for any amino-acid containing constituent. I.e., the molecular weight of the constituent(s) can be used to provide an accurate estimate of the charge density thereof such that the electropherogram peak of the ionic species can be positioned as a unique and defined peak relative to the peak(s) of the constituent(s). By dividing the molecular weight of the amino-acid containing constituent by 100 (the approximate molecular weight of an amino acid); multiplying this value by 20% (the theoretical maximum number of aspartic acid and glutamic acid amino acids in a protein species); and dividing this value by the molecular weight of the constituent, a charge density value for that constituent is provided which can be used for purposes of determining the charge density of the ionic species.

Benzoic acid, having one carboxylic moiety and a molecular weight of 122, has a charge density of 1/122 (0.008) which is greater than the charge density of HSA (0.002).

Example II

Ionic Species Amount Determination

As previously outlined, the amount of the ionic species added to the sample can be determined as follows:

$$(S * D * P.W.) * X/Y$$

Definitions for each factor in the equation are fully detailed above. A most preferred ionic species is benzoic acid. As noted, the most preferred value for S is 30%. For the analysis of serum, a most preferred dilution factor is 1:50 (0.02). The protein concentration of human serum is about 60 mg/ml. The absorbance values for the defined amounts of benzoic acid and the sample (100 μl), measured at a fixed wavelength of 214 nm, were 0.4471(X) and 1.66(Y), respectively; therefore, the quotient is 0.2693 (0.4471/1.66). Accordingly, the concentration (and hence amount) of benzoic acid in the sample is derived as follows:

$$(0.30 * 0.02 * 60) * 0.2693 = 0.097 \text{ mg/ml}$$

For the examples to follow, this value was rounded upwards such that the concentration of benzoic acid in the ionic species was 0.10 mg/ml.

Example III

Protein Control

CZE

Figure 2:
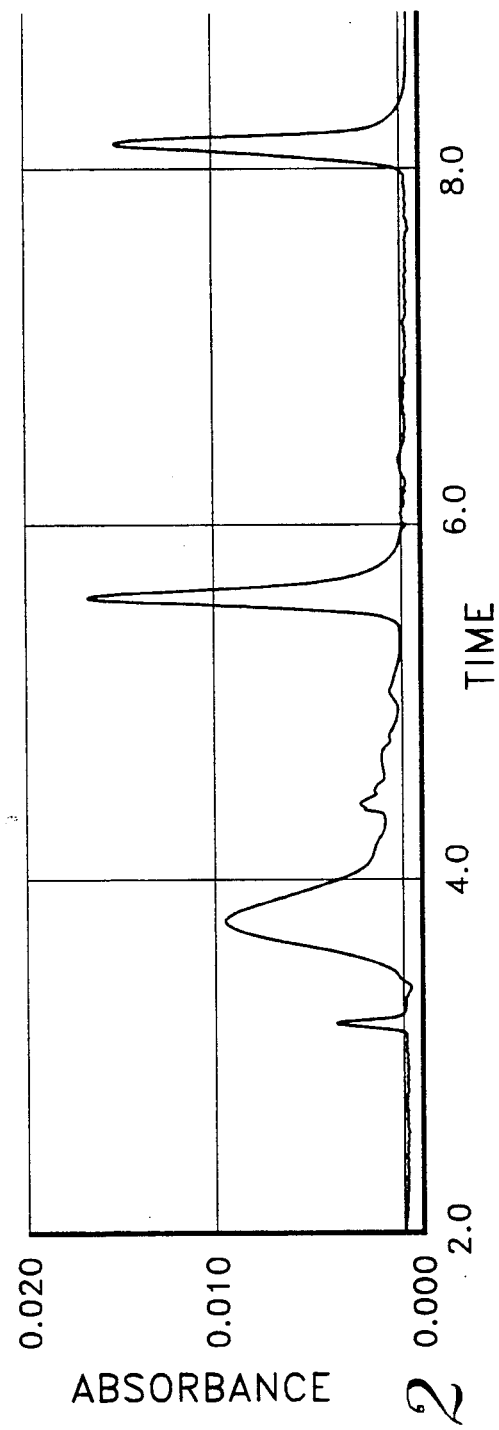
FIG. 2 is an electropherogram of a abnormal serum protein control to which the external markers of FIG. 1 have been added, separated into its constituent parts.
Figure 3:
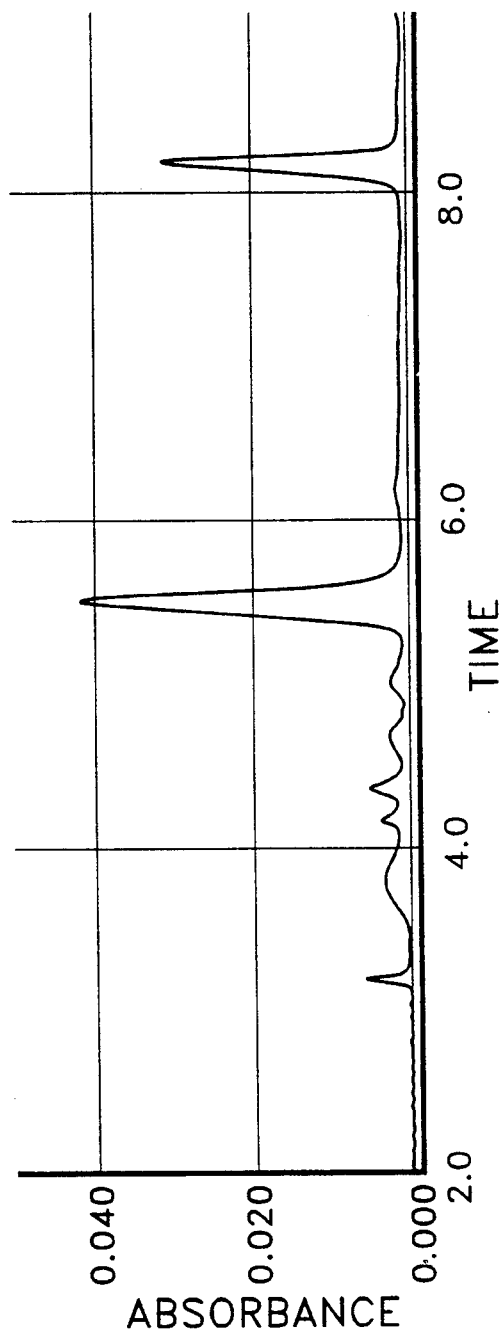
FIG. 3 is an electropherogram of a normal patient serum sample to which the external markers of FIG. 1 have been added, separated into its constituent parts.
Figure 4:
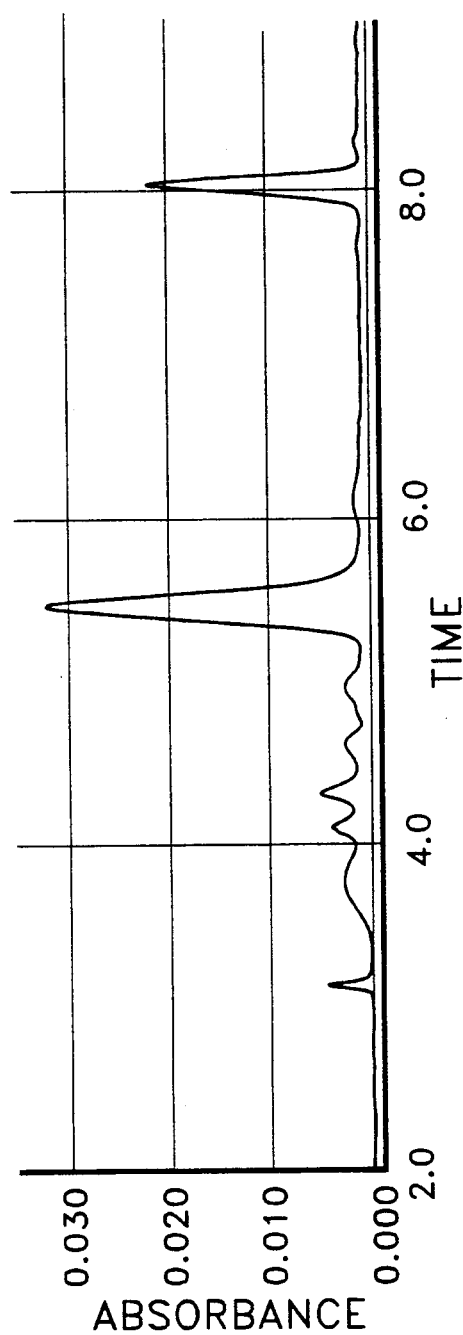
FIG. 4 is an electropherogram of another normal patient serum sample to which the external markers of FIG. 1 have been added, separated into its constituent parts.
Figure 5:
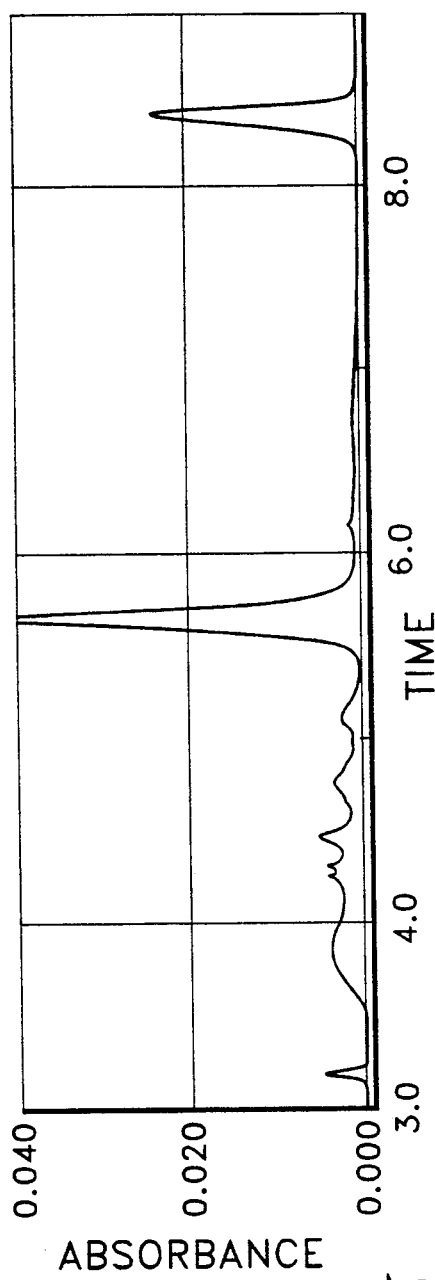
FIG. 5 is an electropherogram of a normal patient serum sample to which the external markers of FIG. 1 have been added, separated into its constituent parts.
Figure 6:
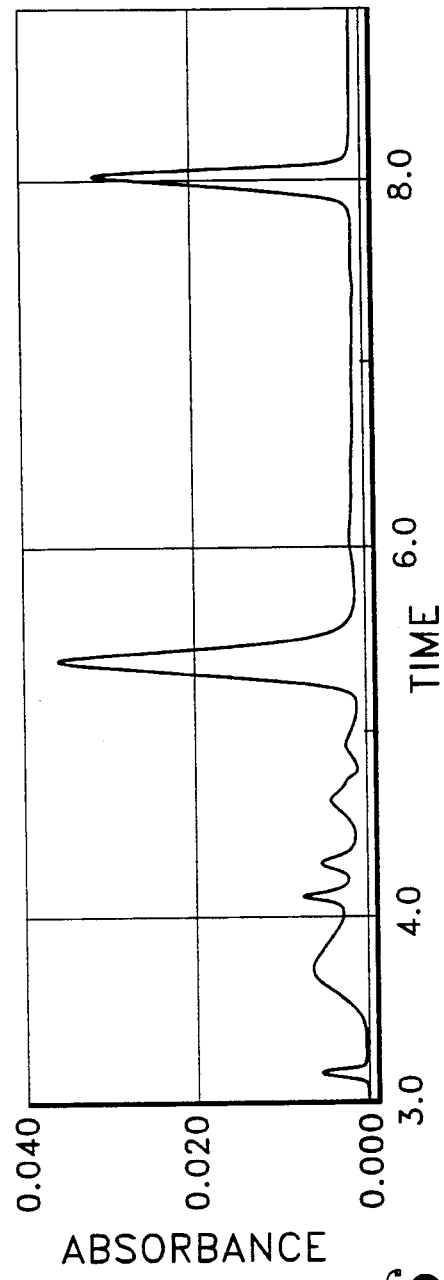
FIG. 6 is an electropherogram of another normal patient serum sample to which the external markers of FIG. 1 have been added, separated into its constituent parts.
Figure 7:
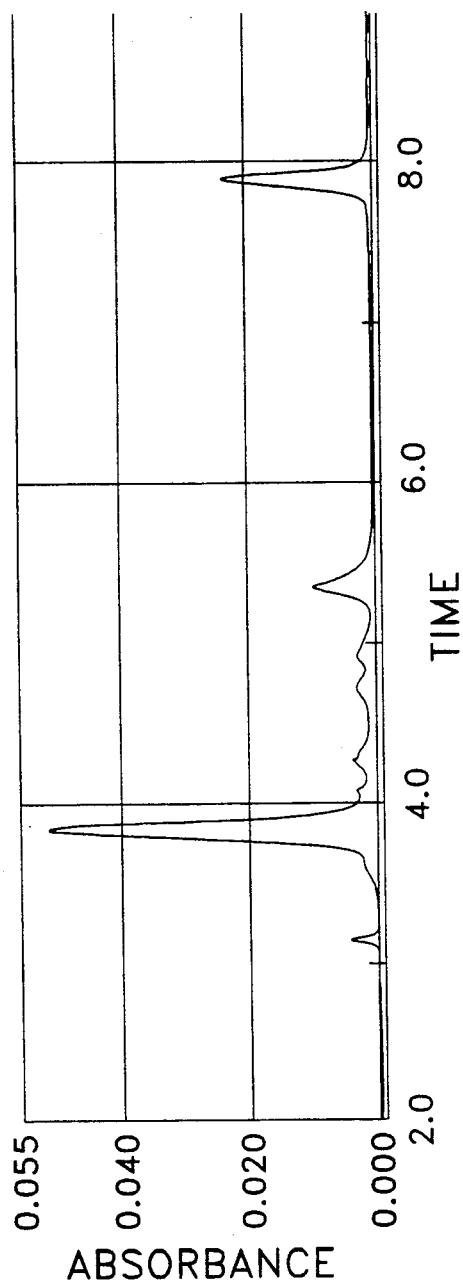
FIG. 7 is an electropherogram of an abnormal patient serum sample having elevated IgG protein level to which the external markers of FIG. 1 have been added, separated into its constituent parts.
Figure 8:
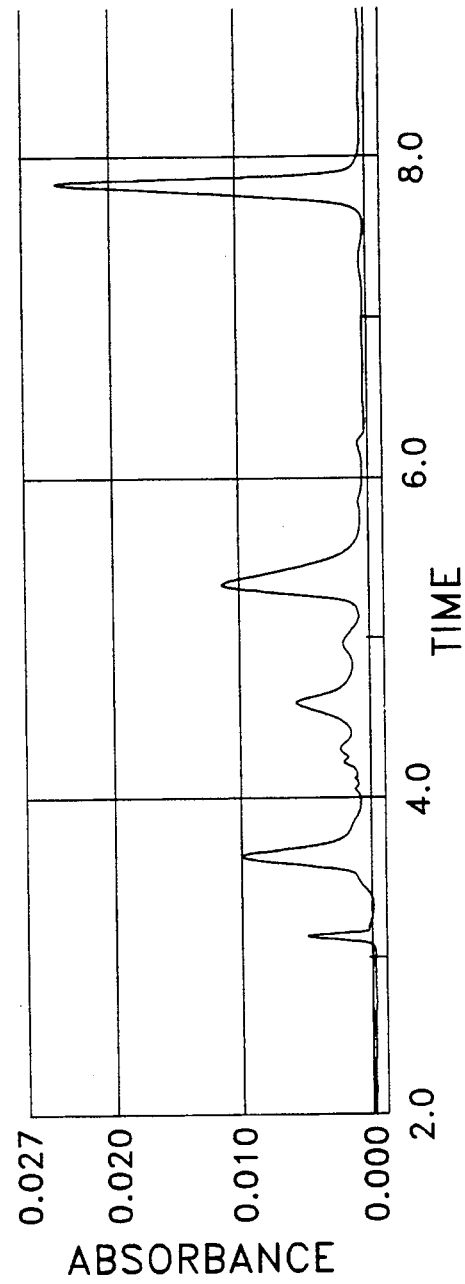
FIG. 8 is an electropherogram of another abnormal patient serum sample having elevated IgA protein level to which the external markers of FIG. 1 have been added, separated into its constituent parts.
Figure 9:
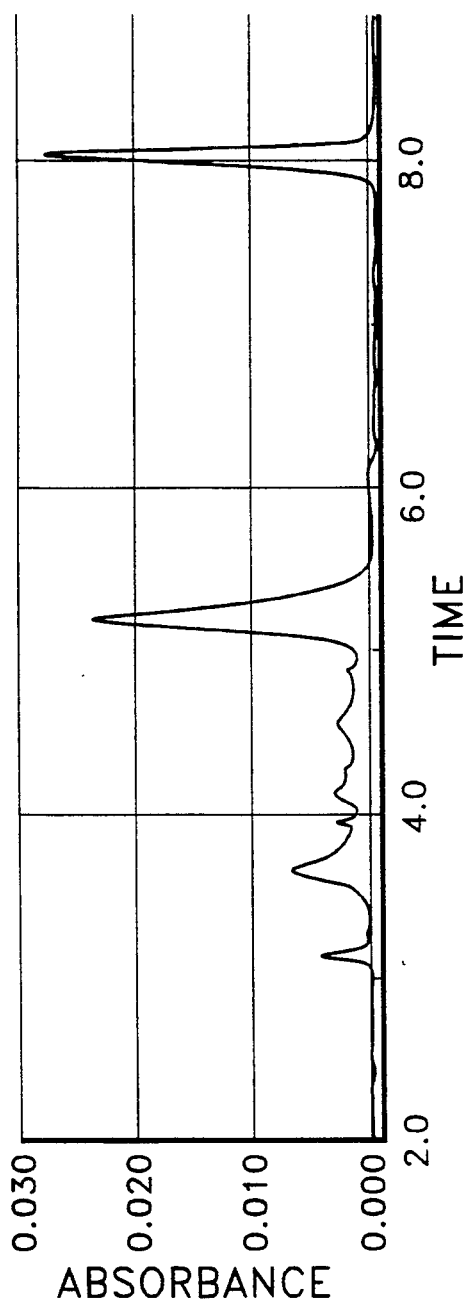
FIG. 9 is an electropherogram of another abnormal patient serum sample having elevated IgM protein level to which the external markers of FIG. 1 have been added, separated into its constituent parts.
Figure 10:
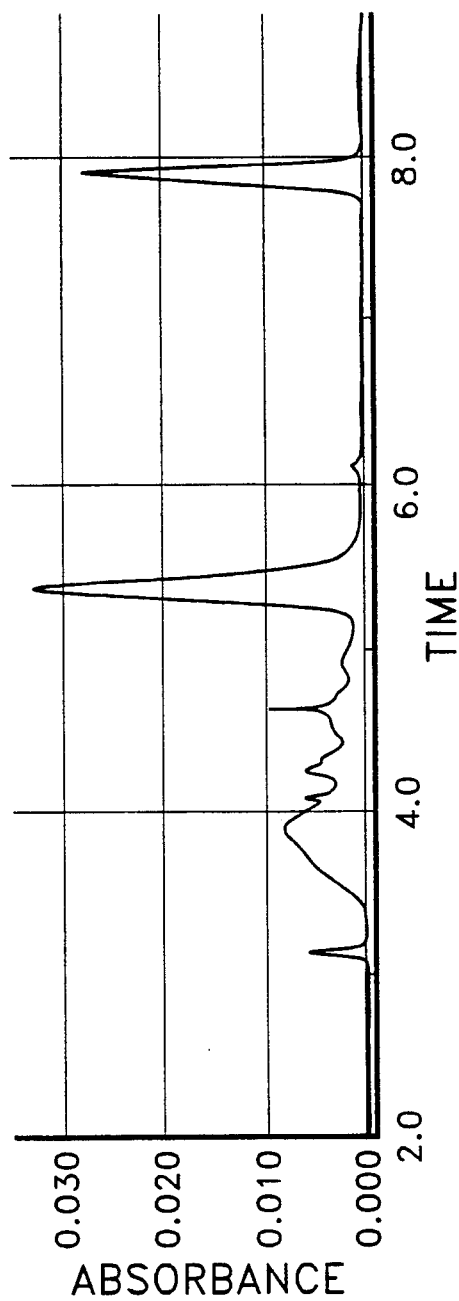
FIG. 10 is an electropherogram of another abnormal patient serum sample having elevated IgM protein level to which the external markers of FIG. 1 have been added, separated into its constituent parts.

The aforementioned protein controls were analyzed using the aforementioned Beckman high performance capillary zone electrophoresis system, with detection at 214 nm and an applied potential of 5 kV. Analytical results were obtained in less than 10 minutes. The analysis produced the electropherogram in FIG. 1 (a normal) and FIG. 2 (abnormal). The abnormal electropherogram peak for gammaglobulin is much higher and wider than the same peak for the normal control. This has the affect of shifting the location of electropherogram peaks for subsequent species and the ionic species relative to the normal control. Additionally, the neutral charge species appears at approximately the same location on both electropherograms, irrespective of the abnormal protein concentration of the abnormal control.

For these and subsequent Examples, the migration times for each electropherogram peak are presented in Table I.

Example IV

Patient Serum

CZE

Eight patient serum samples (1-8) were analyzed in accordance with the procedure outlined in Example III.

For patient samples 1-4, these were all obtained from healthy individuals. Patient samples 5-8, however, exhibited increased (abnormal) immunoglobulin concentrations. Migration times are presented in Table I.

TABLE I

| | Constituent Species' Migration Times | | | | | | |
|---|---|---|---|---|---|---|---|
| | Constituent Species | | | | | | |
| Sample | R | A | B | C | D | E | S |
| Normal | 3.100 | 3.663 | 4.213 | 4.548 | 4.870 | 5.272 | 7.699 |
| Abnormal | 3.179 | 3.763 | 4.422 | 4.714 | 5.069 | 5.553 | 8.138 |
| 1 | 3.192 | 3.801 | 4.346 | 4.688 | 5.005 | 5.462 | 8.176 |
| 2 | 3.141 | 3.775 | 4.308 | 4.612 | 4.967 | 5.424 | 8.024 |
| 3 | 3.201 | 3.861 | 4.329 | 4.774 | 5.122 | 5.641 | 8.380 |
| 4 | 3.570 | 4.020 | 4.640 | 5.020 | 5.300 | 5.660 | 8.210 |
| 5 | 3.129 | 3.721 | 4.283 | 4.726 | 4.929 | 5.335 | 2.891 |
| 6 | 3.129 | 3.623 | 4.283 | 4.599 | 4.955 | 5.322 | 7.821 |
| 7 | 3.121 | 3.629 | 4.257 | 4.625 | 4.904 | 5.310 | 7.884 |
| 8 | 3.141 | 3.661 | 4.143 | 4.574 | 4.879 | 5.283 | 8.024 |

R = neutral charge species (DMF)
A = gammaglobulin
B = beta-1 lipoprotein
C = alpha-2 macroglobulin
D = alpha-1 lipoprotein
E = albumin
S = ionic species (benzoic acid)

As outlined, identification of each constituent species is based upon the "migration ratio" of each species. The migration ratio is defined as the quotient obtained from the value derived from the subtraction of the migration time of the neutral charge species from the migration time of a constituent species, divided by the value derived from subtraction of the migration time of the neutral charge species from the migration time of the ionic species. The migration ratio may be multiplied by 100% so as to provide a migration ratio percentage.

Table II provides the subtracted values described above based upon the migration times set forth in Table I. For Table II, the constituent species are the same as in Table I such that no values are set forth in column R (the neutral charge species). This is because, for consistency, subtraction of the migration time of the neutral charge species from itself is zero.

TABLE II

| Neutral Charge Species' Migration Times Subtracted from Constituent Species' Migration Times | | | | | | | |
|---|---|---|---|---|---|---|---|
| | Constituent Species | | | | | | |
| Sample | R | A | B | C | D | E | S |
| Normal | 0 | .563 | 1.113 | 1.448 | 1.770 | 2.172 | 4.599 |
| Abnormal | 0 | .584 | 1.243 | 1.535 | 1.890 | 2.374 | 4.959 |

TABLE II-continued

| Neutral Charge Species' Migration Times Subtracted from Constituent Species' Migration Times | | | | | | | |
|---|---|---|---|---|---|---|---|
| | Constituent Species | | | | | | |
| Sample | R | A | B | C | D | E | S |
| 1 | 0 | .609 | 1.154 | 1.496 | 1.813 | 2.270 | 4.984 |
| 2 | 0 | .634 | 1.167 | 1.471 | 1.826 | 2.283 | 4.883 |
| 3 | 0 | .660 | 1.128 | 1.573 | 1.921 | 2.440 | 5.179 |
| 4 | 0 | .510 | 1.130 | 1.510 | 1.790 | 2.150 | 4.700 |
| 5 | 0 | .592 | 1.154 | 1.549 | 1.800 | 2.206 | 4.762 |
| 6 | 0 | .494 | 1.154 | 1.470 | 1.826 | 2.193 | 4.692 |
| 7 | 0 | .508 | 1.136 | 1.504 | 1.783 | 2.189 | 4.763 |
| 8 | 0 | .520 | 1.002 | 1.433 | 1.738 | 2.142 | 4.883 |

The migration time value in column S of Table II is the value derived from the migration time of the neutral charge species subtracted from the migration time of the ionic species. Stated differently, this is the total migration time between the external markers, and this is the value against which the constituent species are normalized to derive the constituent species migration ratios.

Table III provides the migration ratio percentages for the constituent species, i.e., each constituent series value from Table II is divided by the total migration time between the external markers to obtain the constituent species migration ratios, and these ratios are multiplied by 100% to obtain the constituent species migration ratio percentages. The constituent species of Table III are the same as those in Table I.

TABLE III

| Constituent Species Migration Ratio Percentages | | | | | | | |
|---|---|---|---|---|---|---|---|
| | Constituent Species | | | | | | |
| Sample | R | A | B | C | D | E | S |
| Normal | 0 | 12.24 | 24.20 | 31.49 | 38.49 | 47.23 | 100 |
| Abnormal | 0 | 11.78 | 25.07 | 30.95 | 38.11 | 47.87 | 100 |
| 1 | 0 | 12.22 | 23.15 | 30.02 | 36.38 | 45.55 | 100 |
| 2 | 0 | 12.98 | 23.90 | 30.12 | 37.40 | 46.75 | 100 |
| 3 | 0 | 12.74 | 21.78 | 30.37 | 37.09 | 47.11 | 100 |
| 4 | 0 | 10.85 | 24.04 | 32.13 | 38.09 | 45.74 | 100 |
| 5 | 0 | 12.43 | 24.23 | 32.53 | 37.80 | 46.33 | 100 |
| 6 | 0 | 10.53 | 24.60 | 31.33 | 38.92 | 46.74 | 100 |
| 7 | 0 | 10.67 | 23.85 | 31.59 | 32.43 | 45.96 | 100 |
| 8 | 0 | 10.65 | 20.52 | 29.35 | 35.54 | 4.387 | 100 |

Two points of interest are obtained from the above data. First, using, for example, the normal control as a reference starting point, it is evident that every constituent species from every sample analyzed has the same or substantially the same migration ratio percentage as that normal control constituent species (i.e. going down each column). It is preferred that a sample control having defined concentration ranges for the constituent species be used as the comparative constituent species migration ratio. However, any sample can be used to generate a table of comparative constituent species migration ratios because for same-sample constituent species, the migration ratios will be the same or substantially the same for the same constituent species. Second, because the migration ratios are normalized values, the value difference between two species from the same sample are highlighted (i.e. going across each row). For example, the alpha-2 macroglobulin and alpha-1 lipoprotein migration times for patient sample #4 are 5.020 and 5.300, respectively (see Table I). This evidences an approximate 5% differential. However, the migration ratio percentages for these constituents are accentuated, whereby the values are 32.130% and 38.09%, respectively, evidencing a 15% difference. Thus, the within sample identification of species is enhanced when migration ratios are derived.

As the above results demonstrate, sample constituents can be accurately and rapidly identified by CZE using the external markers as disclosed herein. Accordingly, the foregoing data demonstrates the advantages and benefits which are derived from CZE analysis of samples utilizing at least two external markers for the identification of sample constituent species.

Based upon the foregoing, a constituent species identification reference can be generated. For example, the migration ratio percentage values for both the normal and abnormal controls provide a reference against which migration ratios from human serum constituent species can be compared to identify each constituent species from the sample. As used herein, the term "reference" includes, but is not limited to, migration ratios as transcribed electronically on, for example, a computer-based medium, or as transcribed on, for example, paper charts and the like.

While the foregoing external markers and methodology have been described in considerable detail and in terms of preferred embodiments, these are not to be construed as limitations on the disclosure or the claims that follow. For example, the methodology is applicable to forensic DNA identification whereby the external markers are added to a DNA-containing sample and an electropherogram is obtained. This, then, would be followed by analysis of a DNA-sample obtained from an individual suspected of being the source of the original DNA-sample. If the migration ratios are the same or substantially the same for both analyzed samples, then that individual may be the source of the original DNA-sample. Similarly, the foregoing methodology can be applied to parental-matching identification whereby a DNA-sample from an offspring and a suspected parent could be analyzed as described such that the same or substantially the same migration ratios for the analyzed samples may be indicative of a genetic link between the tested individuals.

Furthermore, by subjecting a protein derived from recombinant DNA techniques and a natural/wild type protein to the disclosed method, and then determining the migration ratios for each, one can determine if the recombinantly derived protein is the same or substantially the same as the natural/wild type protein. Because proteins derived from recombinant DNA techniques must perform the same function as their natural/wild type protein counterparts, the present methodology can be used, e.g., as a screening procedure to determine if the recombinantly derived proteins are the same or substantially the same as the natural/wild type protein.

The invention is not to be limited to the particular Beckman high performance capillary electrophoresis system described. Modifications and changes that are within the purview of those skilled in the art are intended to fall within the scope of the following claims.

What is claimed is:

1. A method of identifying constituent species in a sample by capillary zone electrophoresis comprising the following steps:
   a) adding at least one external ionic species and at least one external neutral charged species to the sample to form a mixture;
   b) subjecting the mixture to capillary zone electrophoresis;
   c) detecting the external ionic species, external neutral charged species and any constituent species in said mixture;
   d) determining a migration ratio for at least one constituent species; and
   e) identifying the constituent species based upon said migration ratio.

2. The method of claim 1 wherein migration times for the ionic species, the neutral charged species and any constituent species in the mixture are detected.

3. The method of claim 1 wherein electropherogram peaks for the ionic species, the neutral charged species and any constituent species in the mixture are detected.

4. The method of claim 2 wherein the migration ratio is determined by subtracting the migration time of the neutral charged species from the migration time of the constituent species to obtain a first value; subtracting the migration time of the neutral charged species from the migration time of the ionic species to obtain a second value; and mathematically dividing the first value by the second value to obtain the migration ratio.

5. The method of claim 3 wherein the migration ratio is determined by obtaining a first distance between the electropherogram peak of the ionic species and the electropherogram peak of the neutral charge species; obtaining a second distance between the constituent species and the neutral charge species; and mathematically dividing the second distance by the first distance to obtain the migration ratio.

6. The method of claim 1 wherein said ionic species is soluble in an aqueous medium at pH greater than about 8.00.

7. The method of claim 1 wherein said ionic species has an absorbance of less than about 300 nm.

8. The method of claim 1 wherein said ionic species has a charge density greater than the charge density of the last major constituent of said sample to be detected.

9. The method of claim 1 wherein the concentration of said ionic species added to the sample is determined by multiplying a dilution factor of the sample by a protein weight of a normal-range sample control to obtain a first value; multiplying a desired integrated area percentage of the ionic species by the first value to obtain a second value; and multiplying the second value by a third value, the third value derived by mathematically dividing an absorbance value of a fixed amount of the ionic species measured at a fixed wavelength by an absorbance value of about the same fixed amount of the sample measured at about the same fixed wavelength.

10. The method of claim 9 wherein the desired integrated area percentage is a value less than about 50%.

11. The method of claim 9 wherein the desired integrated area percentage is a value between about 50% and about 40%.

12. The method of claim 9 wherein the desired integrated area percentage is about 0.30.

13. The method of claim 9 wherein the dilution factor is a value between about 0.05 and about 0.01.

14. The method of claim 9 wherein the dilution factor is about 0.02.

15. The method of claim 9 wherein the protein concentration range is from about 10 μg/ml to about 60,000 μg/ml.

16. The method of claim 9 wherein the protein concentration is about 60 mg/ml.

17. The method of claim 1 wherein the charge density of the ionic species is between about 0.02 and about 0.001.

18. The method of claim 1 wherein the ionic species has a charge density between about 0.01 and about 0.004.

19. The method of claim 1 wherein the ionic species comprises at least one negative charge and has a molecular weight of at least about 50.

20. The method of claim 1 wherein said ionic species is selected from the group consisting of formic acid, acetic acid, benzo-phosphoric acid, propionic acid, isopropionic acid, butyric acid, isobutyric acid, benzoic acid, benzo-sulfonic acid, ortho-chloro benzoic acid, meta-chloro benzoic acid, para-chloro benzoic acid, naphthyl sulfonic acid, benzo naphthalinic acid, chlorobenzo naphthalinic acid, chloro-naphthyl sulfonic acid, tetra-iodo benzo naphthyl sulfonic acid, and di-iodo anthracenyl sulfonic acid.

21. The method of claim 1 wherein said ionic species is benzoic acid.

22. The method of claim 24 wherein the concentration of said benzoic acid in said sample is about 0.10 mg/ml.

23. The method of claim 1 wherein said neutral charge species has absorbance characteristics substantially similar to the absorbance characteristics of peptide bonds.

24. The method of claim 1 wherein said neutral charge species has an absorbance of less than about 300 nm.

25. The method of claim 1 wherein said neutral charge species is soluble in an aqueous medium at pH greater than about 8.00.

26. The method of claim 1 wherein the concentration of said neutral charge species in said mixture is up to about 0.050% by volume.

27. The method of claim 1 wherein said neutral charge species is selected from the group consisting of mesityl oxide, isopropanol, methanol, ethanol, ethylene glycol, dimethylformamide (DMF), formamide, protected peptides and protected amino acids.

28. The method of claim 1 wherein said neutral charge species is DMF.

29. A method of generating ionic species migration ratios for sample constituent species by capillary zone electrophoresis comprising the following steps:
a) adding at least one ionic species and at least one neutral charge species to the sample to form a mixture;
b) analyzing said mixture by capillary zone electrophoresis;
c) detecting the ionic species, neutral charge species and any constituent species in said mixture;
d) determining a migration ratio for at least one constituent species; and
e) repeating step (d) for each constituent species of the sample.

30. The method of claim 29 wherein migration times for the ionic species, neutral charged species and any constituent species in the mixture are detected.

31. The method of claim 29 wherein electropherogram peaks for the ionic species, the neutral charged species and any constituent species in the mixture are detected.

32. The method of claim 30 wherein the migration ratio is determined by subtracting the migration time of the neutral charged species from the migration time of the constituent species to obtain a first value; subtracting the migration time of the neutral charged species from the migration time of the ionic species to obtain a second value; and mathematically dividing the first value by the second value to obtain the migration ratio.

33. The method of claim 31 wherein the migration ratio is determined by obtaining a first distance between the electropherogram peak of the ionic species and the electropherogram peak of the neutral charge species; obtaining a second distance between the constituent species and the neutral charge species; and mathematically dividing the second distance by the first distance to obtain the migration ratio.

34. The method of claim 29 wherein said ionic species is selected from the group consisting of formic acid, acetic acid, benzo-phosphoric acid, propionic acid, isopropionic acid, butyric acid, isobutyric acid, benzoic acid, benzo-sulfonic acid, ortho-chloro benzoic acid, meta-chloro benzoic acid, para-chloro benzoic acid, naphthyl sulfonic acid, benzo naphthalinic acid, chlorobenzo naphthalinic acid, chloro-naphthyl sulfonic acid, tetra-iodo benzo naphthyl sulfonic acid, and di-iodo anthracenyl sulfonic acid.

35. The method of claim 29 wherein said neutral charge species marker is selected from the group consisting of mesityl oxide, isopropanol, methanol, ethanol, ethylene glycol, dimethylformamide (DMF), formamide, protected peptides and protected amino acids.

36. The method of claim 29 wherein the sample is selected from the group consisting of whole blood, plasma, serum, urine, cerebrospinal fluid, mammalian DNA, mammalian RNA, and proteins derived from recombinant DNA techniques.

* * * * *